USO10928346B2

(12) United States Patent
Logan et al.

(10) Patent No.: US 10,928,346 B2
(45) Date of Patent: Feb. 23, 2021

(54) MULTI-ELEMENT SENSORS

(71) Applicant: DENSO International America, Inc., Southfield, MI (US)

(72) Inventors: Jonathan Logan, Walled Lake, MI (US); Michael Lewis, Dearborn, MI (US); Rafal Kaput, Sterling Heights, MI (US); Blaise Friery, Farmington Hills, MI (US)

(73) Assignee: DENSO International America, Inc., Southfield, MI (US)

( * ) Notice: Subject to any disclaimer, the term of this patent is extended or adjusted under 35 U.S.C. 154(b) by 359 days.

(21) Appl. No.: 16/057,321

(22) Filed: Aug. 7, 2018

(65) Prior Publication Data

US 2020/0049646 A1 Feb. 13, 2020

(51) Int. Cl.
*G01N 27/12* (2006.01)
*G01N 27/407* (2006.01)
*B01D 53/94* (2006.01)
*F01N 13/00* (2010.01)
*G01N 33/00* (2006.01)

(52) U.S. Cl.
CPC ....... *G01N 27/125* (2013.01); *B01D 53/9495* (2013.01); *F01N 13/008* (2013.01); *F01N 13/009* (2014.06); *G01N 27/407* (2013.01); *F01N 2560/025* (2013.01); *F01N 2560/026* (2013.01); *F01N 2560/14* (2013.01); *G01N 33/0037* (2013.01)

(58) Field of Classification Search
CPC ............ G01N 27/125; G01N 33/0037; B01D 53/9495; F01N 13/009; F01N 13/008; F01N 2560/14; F01N 2560/025; F01N 2560/026; F01N 3/10; Y02A 50/20
See application file for complete search history.

(56) References Cited

U.S. PATENT DOCUMENTS

2015/0041334 A1* 2/2015 Matsuoka ............ F02D 41/0235
205/775
2017/0205314 A1* 7/2017 McQuillen ......... G01N 27/4175

FOREIGN PATENT DOCUMENTS

JP H06265495 A 9/1994

* cited by examiner

*Primary Examiner* — Suman K Nath
(74) *Attorney, Agent, or Firm* — Harness, Dickey & Pierce, P.L.C.

(57) ABSTRACT

A sensor probe having a first sensing element and a second sensing element. The first sensing element generates current changes in response to changes in a relative amount of a target element present in reference air versus a first exhaust gas chamber of the sensor probe. A second sensing element generates current changes in response to changes in a relative amount of the target element present in the first exhaust gas chamber and either a second exhaust gas chamber of the sensor probe or reference air.

20 Claims, 3 Drawing Sheets

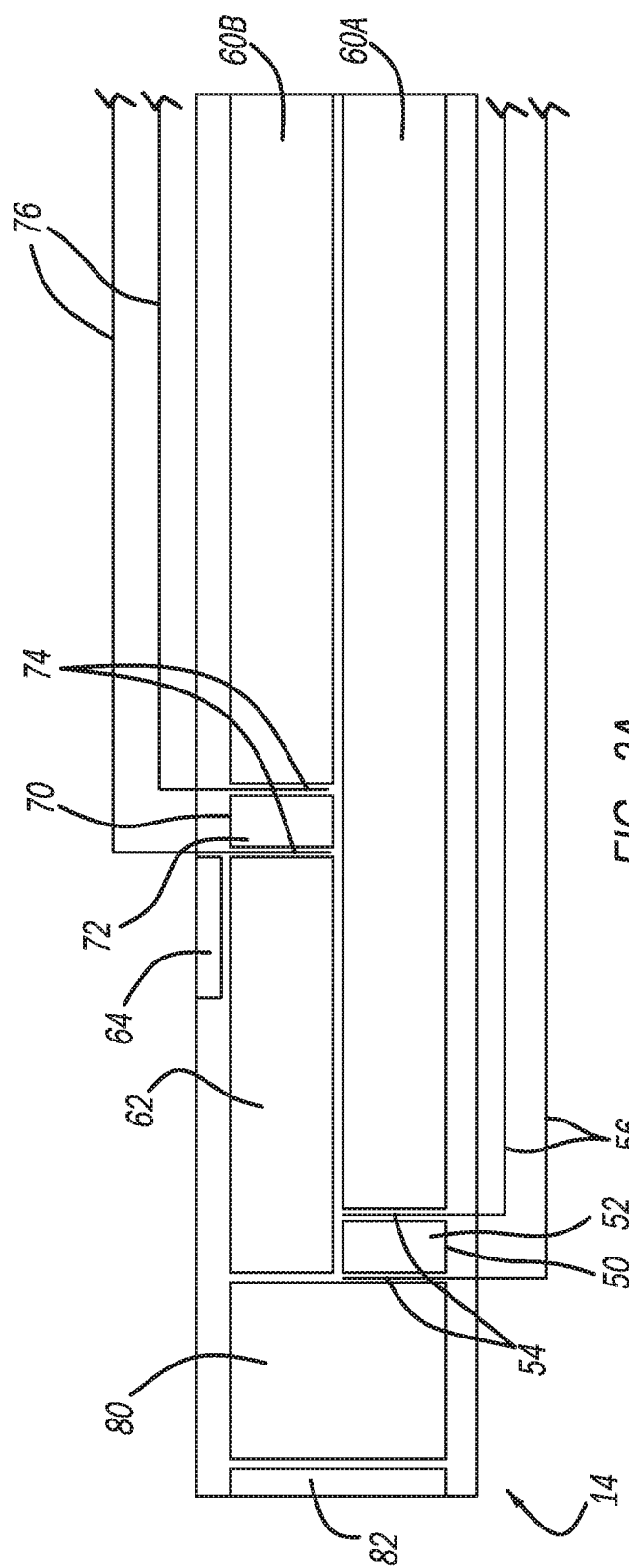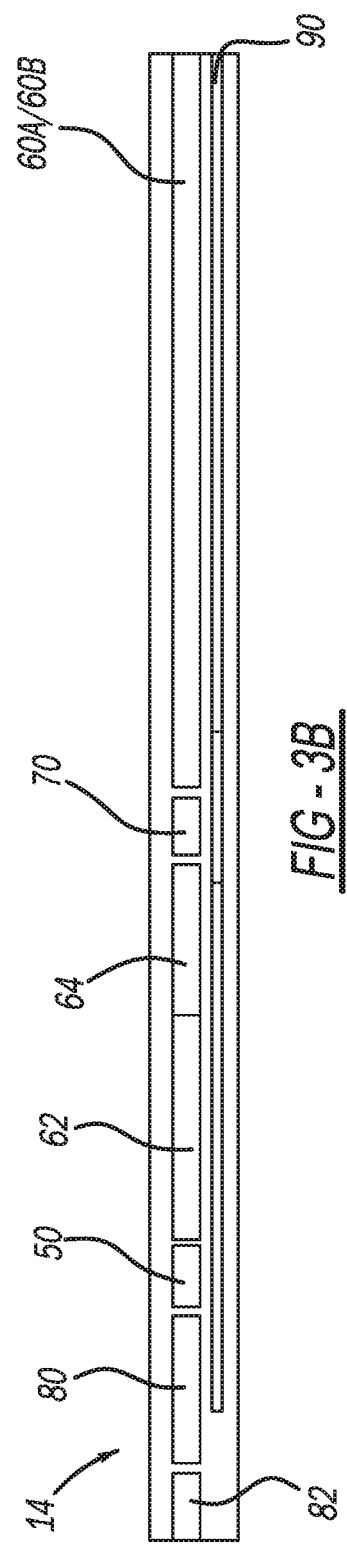

MULTI-ELEMENT SENSORS

FIELD

The present disclosure relates to multi-element sensors, such as multi-element exhaust sensors.

BACKGROUND

This section provides background information related to the present disclosure, which is not necessarily prior art.

Vehicle exhaust systems typically include sensors for measuring the amount of a target element present in the vehicle's exhaust, such as the amount of oxygen and/or $NO_x$. In a typical exhaust system, a first sensor probe is arranged in the exhaust flow before a catalyst brick of a catalytic converter, and a second sensor probe is arranged after the catalyst brick. Thus two sensor probes are typically used. While such a dual sensor probe arrangement is suitable for its intended use, it is subject to improvement. For example, it would be desirable to reduce the cost and installation time of the sensor probe arrangement. The present disclosure advantageously eliminates the need for the current dual sensor probe arrangement, thereby reducing costs and installation time.

SUMMARY

This section provides a general summary of the disclosure, and is not a comprehensive disclosure of its full scope or all of its features.

The present disclosure includes a sensor probe having a first sensing element and a second sensing element. The first sensing element generates current changes in response to changes in a relative amount of a target element present in reference air versus a first exhaust gas chamber of the sensor probe. The second sensing element generates current changes in response to changes in a relative amount of the target element present in the first exhaust gas chamber and either a second exhaust gas chamber of the sensor probe or reference air.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of select embodiments and not all possible implementations, and are not intended to limit the scope of the present disclosure.

FIG. 3A is a top view of another exemplary probe tip for the sensor probe of FIG. 1;

FIG. 3B is a side view of the probe tip of FIG. 3A;

Corresponding reference numerals indicate corresponding parts throughout the several views of the drawings.

DETAILED DESCRIPTION

Example embodiments will now be described more fully with reference to the accompanying drawings.

Figure 1:
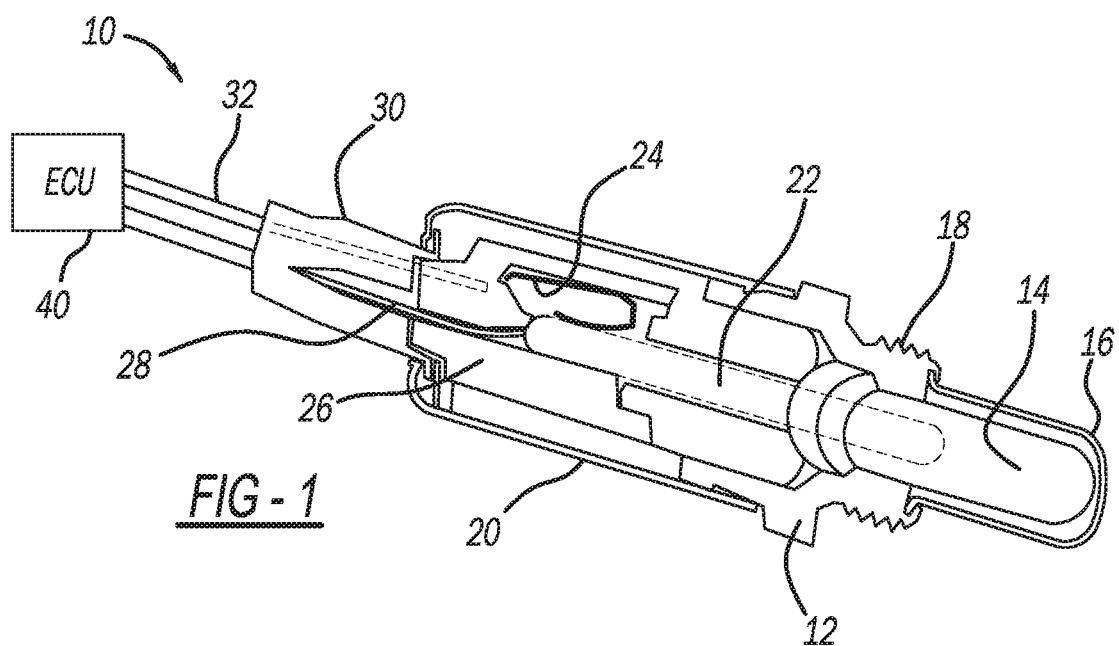
FIG. 1 is a perspective view of a sensor probe according to the present disclosure.

FIG. 1 illustrates a sensor probe in accordance with the present disclosure for sensing the presence of a target element in exhaust gas of any suitable engine. Suitable engines include any suitable vehicle engine, such as the engine of any suitable passenger vehicle, commercial vehicle, mass transit vehicle, military vehicle/equipment, construction vehicle/equipment, watercraft, aircraft, etc. The sensor probe 10 may be installed in the exhaust system of any suitable non-vehicle engine as well, such as any suitable generator.

The sensor probe 10 includes a sensor housing 12 housing a probe tip 14. The probe tip 14 is covered by a gas permeable cover 16. An exterior of the housing 12 includes threads 18 for mounting the sensor probe 10 at any suitable location of an exhaust system. The sensor probe 10 further includes a shell 20, inside of which is a heater 22, and a heater contact 24. An insulating bushing 26 extends around the heater 22 and the heater contact 24. Reference air is introduced into the sensor probe 10 through a reference air inlet 28.

Extending from an end of the sensor probe 10 opposite to the sensor housing 12 is a cable connector 30. Extending through the cable connector 30 are wire leads 32, which include leads for the heater 22 and the sensing elements described herein. The wire leads 32 extend to any suitable engine control unit 40, which controls various engine functions and monitors an engine exhaust system, such as the effectiveness of catalyst brick 160 (FIGS. 4 and 5) as described herein.

Figure 2A:
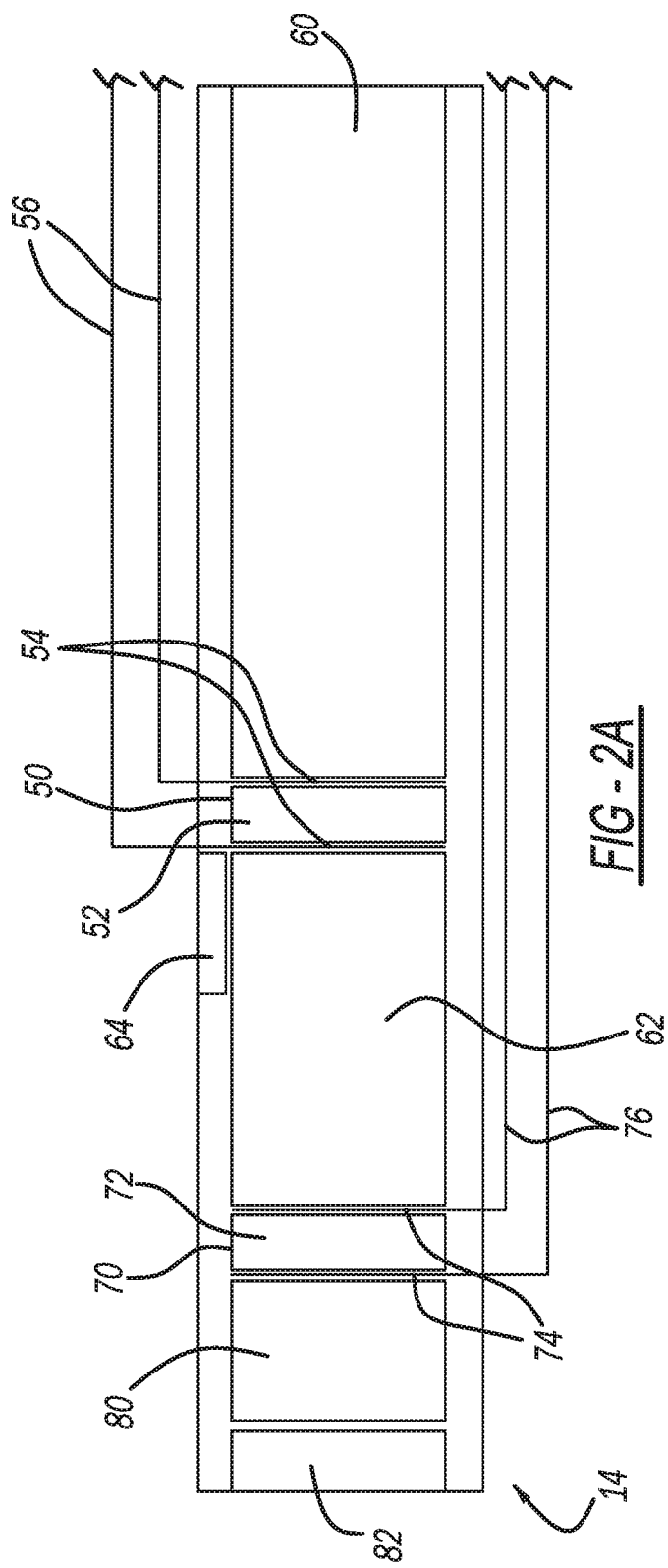
FIG. 2A is a top view of an exemplary probe tip for the sensor probe of FIG. 1.
Figure 2B:
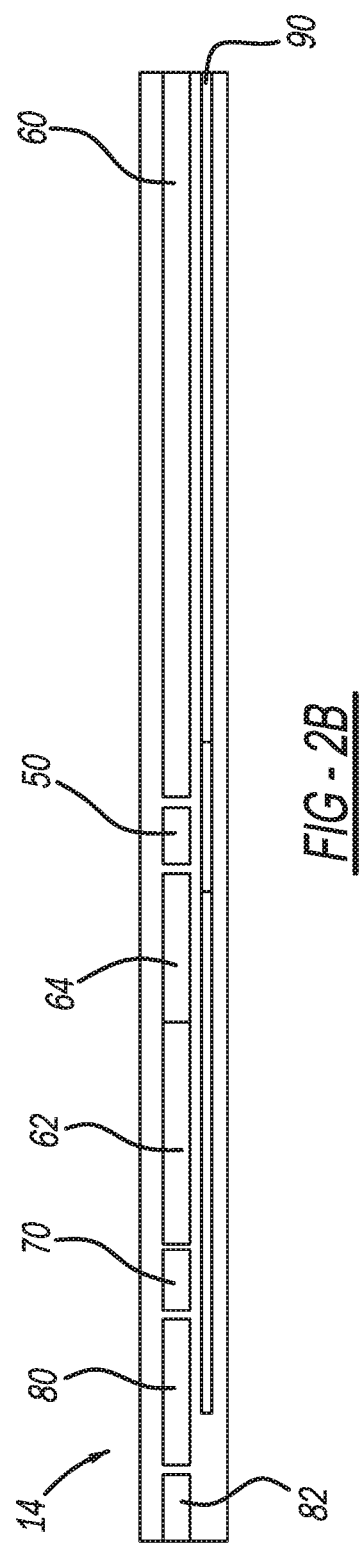
FIG. 2B is a side view of the probe tip of FIG. 2A.

FIGS. 2A and 2B illustrate an exemplary probe tip 14 for the sensor probe 10. The probe tip 14 generally includes a sensing element 50 having a membrane 52 and gas permeable electrodes 54 on opposite sides of the membrane 52. The membrane 52 may be any suitable sensor membrane, such as a ceramic membrane including zirconia. The membrane 52 is plated on opposite sides with the gas permeable electrodes 54, which may be porous platinum electrodes, for example. Extending from the gas permeable electrodes 54 are wire leads 56, which are included with the wire leads 32 extending to the ECU 40.

The sensing element 50 is between a reference air chamber 60 and a pre-catalyst exhaust gas chamber 62 of the probe tip 14. Reference air enters the reference air chamber 60 through the reference air inlet 28 (FIG. 1), and exhaust gas enters the pre-catalyst exhaust gas chamber 62 through a diffusion layer 64. The current across the sensing element 50 changes based on the relative amount of a target element present in the reference air chamber 60 versus the pre-catalyst exhaust gas chamber 62. Based on the current measured across membrane 52, which is input to the ECU 40 by way of the wire leads 56, the ECU (ASIC) 40 converts the current to a voltage output and is configured to identify how much of the target element is present in the reference air chamber 60 versus in the pre-catalyst exhaust gas chamber 62. The target element may be any suitable target element, such as oxygen or $NO_x$ for example.

The probe tip 14 further includes another sensing element 70. The sensing element 70 includes a membrane 72 and gas permeable electrodes 74.

The membrane 72 may be a zirconia membrane and the gas permeable electrodes 74 may be porous, platinum electrodes, for example. Extending from the gas permeable electrodes 74 are wire leads 76, which are included with the wire leads 32. The sensing element 70 is arranged between the pre-catalyst exhaust gas chamber 62 and a post-catalyst exhaust gas chamber 80 of the probe tip 14. The probe tip 14 includes a diffusion layer 82, through which exhaust gas flows to the post-catalyst exhaust gas chamber 80. The sensing element 70 generates current changes in response to changes in a relative amount of a target element present in the pre-catalyst exhaust gas chamber 62 versus the post-catalyst exhaust gas chamber 80. The target element may be the same target element that the sensing element 50 is configured to detect, or any other suitable target element. Exemplary target elements include oxygen and $NO_x$.

The probe tip 14 further includes a heating element 90. The heating element 90 is part of the heater 22, which receives voltage from heater contact 24. The heating element 90 extends to the sensing elements 50 and 70 to heat the sensing elements 50 and 70 and improve the responsiveness thereof.

With additional reference to FIGS. 3A and 3B, the probe tip 14 may be configured in an alternate manner. Specifically, the sensing element 50 may be alternatively arranged between a reference air chamber 60A and the post-catalyst exhaust gas chamber 80. The sensing element 70 may be arranged between a second reference air chamber 60B and the pre-catalyst exhaust gas chamber 62. Although the reference air chambers 60A and 60B are illustrated in FIG. 3A as two separate chambers, in some applications the reference air chambers 60A and 60B may be a single reference air chamber.

Figure 4:
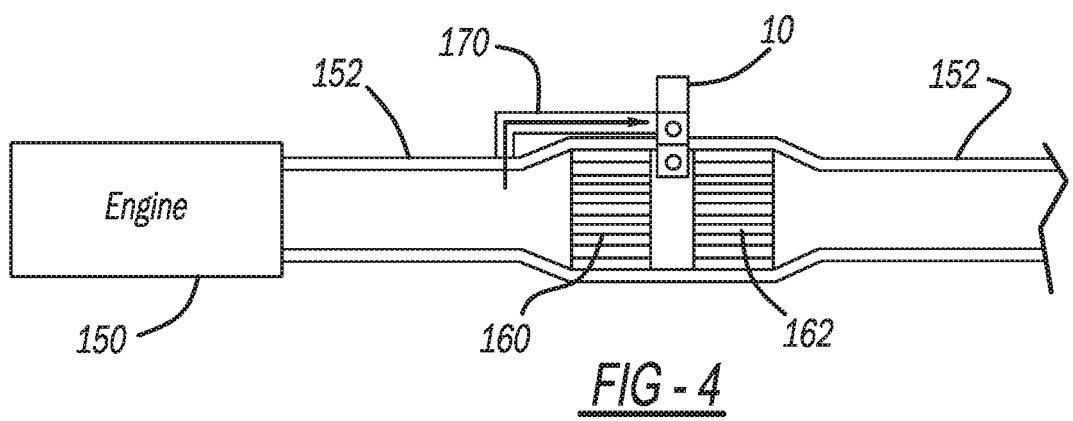
FIG. 4 illustrates the sensor probe of FIG. 1 installed in an exemplary exhaust system, the sensor probe including the probe tip of FIGS. 2A and 2B.

FIG. 4 illustrates the sensor probe 10 installed in an exemplary exhaust system of an engine 150. The exhaust system includes an exhaust conduit 152 housing a first catalyst brick 160 and a second catalyst brick 162. The sensor probe 10 is arranged between the first catalyst brick 160 and the second catalyst brick 162. A bypass 170 of the exhaust conduit 152 extends to the sensor probe 10 (such as to the diffusion layer 64) from an area of the exhaust conduit 152 upstream (relative to exhaust gas flow from the engine 150 through the exhaust conduit 152) of the first catalyst brick 160. Thus some of the exhaust flowing from the engine 150 flows through the first catalyst brick 160, and some of the exhaust flows through the bypass 170 to bypass the first catalyst brick 160. Exhaust gas from the bypass 170 enters the pre-catalyst exhaust gas chamber 62 through the diffusion layer 64. Thus the sensor probe 10 is advantageously able to measure the amount of the target element present in exhaust gas from the engine 150 that has not been treated by the first catalyst brick 160 relative to the amount of the target element in the reference air (ambient air) present in the reference air chamber 60.

The sensor probe 10 is also able to measure the relative amount of the target element present in exhaust that has been treated by the first catalyst brick 160 versus the exhaust that has not been treated by the first catalyst brick 160. Exhaust that has been treated by the first catalyst brick 160 enters the post-catalyst exhaust gas chamber 80 through the diffusion layer 82. The position of the sensing element 70 between the pre-catalyst exhaust gas chamber 62 and the post-catalyst exhaust gas chamber 80 results in the sensing element 70 generating current changes based on the relative levels of the target element in the chambers 62 and 80.

Figure 5:
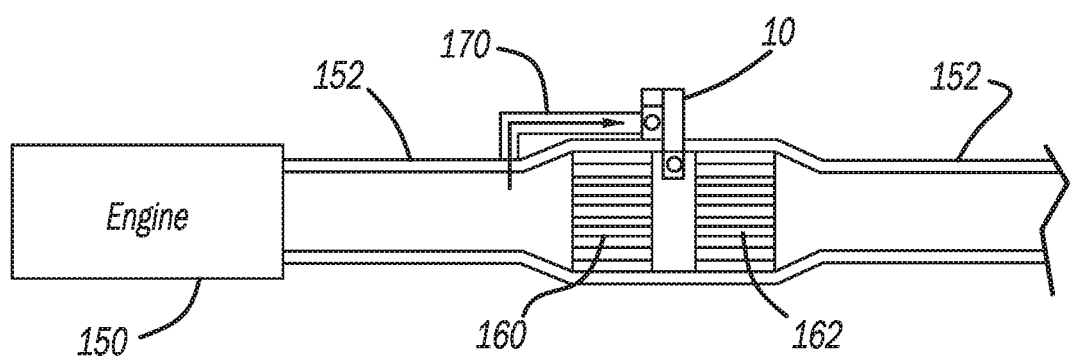
FIG. 5 illustrates the sensor probe of FIG. 1 installed in an exemplary exhaust system, the sensor probe including the probe tip of FIGS. 3A and 3B.

With reference to FIG. 5, the sensor 10 including the sensor probe tip 14 of FIGS. 3A and 3B is illustrated as installed in the exhaust conduit 152 between the first catalyst brick 160 and the second catalyst brick 162. The bypass 170 extends to the probe tip 14 to direct pre-catalyst exhaust gas to the pre-catalyst exhaust gas chamber 62 through the gas diffusion layer 64. Exhaust gas that has passed through the first catalyst brick 160 enters the post-catalyst exhaust gas chamber 80 through the diffusion layer 82. Thus with the probe tip 14 of FIG. 3A and FIG. 3B, the sensing element 50 generates current changes based on the relative amount of the target element in the reference air of reference air chamber 60A versus the exhaust gas in the post-catalyst exhaust gas chamber 80. The sensing element 70 generates current changes based on the relative amount of the target element present in the reference air of reference air chamber 60B versus the exhaust gas of the pre-catalyst exhaust gas chamber 62.

The present disclosure thus advantageously provides for a single sensor probe including multiple sensing elements 50 and 70 that generate changes in current corresponding to the relative amount of a target element in exhaust gas that has not passed through the first catalyst brick 160 and reference ambient air, as well as relative to exhaust gas that has passed through the first catalyst brick 160. With respect to the probe tip 14 of FIG. 3A and FIG. 3B, the relative amount of the target element present in reference air as compared to the amount of the target element present in exhaust gas that has passed through the first catalyst brick 160 can also be measured with a single sensor probe. The present teachings thus advantageously eliminate the need for two sensor probes, such as a sensor probe present in the exhaust conduit 152 before the first catalyst brick 160 and after the first catalyst brick 160.

Thus the sensor probe 10 advantageously measures the relative amount of the target element in exhaust that has been treated by the first catalyst brick 160 and exhaust that has not been treated by the first catalyst brick 160. The currents of the sensing elements 50 and 70 are input to the ECU 40 by way of wire leads 32. Based on the currents, the ECU 40 monitors the effectiveness of the first catalyst brick 160 and is configured to generate any suitable alerts to an operator of the vehicle to notify the operator that the first catalyst brick 160 needs replacement.

The present disclosure advantageously provides for a sensor probe 10 that reduces costs and expands the available sensor readings/outputs, such as to the following: the relative amount of the target element present in the reference air chamber 60 versus the pre-catalyst exhaust gas chamber 62; the relative amount of the target element present in the pre-catalyst exhaust gas chamber 62 versus the post-catalyst exhaust gas chamber 80; and the amount of the target element present in the reference air chamber 60A versus the post-catalyst exhaust gas chamber 80.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A sensor probe comprising:
   a first sensing element that generates current changes in response to changes in a relative amount of a target element present in reference air versus a first exhaust gas chamber of the sensor probe; and
   a second sensing element that generates current changes in response to changes in a relative amount of the target element present in the first exhaust gas chamber and a second exhaust gas chamber of the sensor probe;
   wherein the sensor probe is a single probe including both the first sensing element and the second sensing element.

2. The sensor probe of claim 1, wherein the target element is oxygen.

3. The sensor probe of claim 1, wherein the target element is $NO_x$.

4. The sensor probe of claim 1, wherein the first sensing element and the second sensing element both include a zirconia membrane coated with gas permeable electrodes on opposite sides thereof.

5. The sensor probe of claim 1, wherein the first sensing element is between a reference air chamber and the first exhaust gas chamber in receipt of exhaust gas that has yet to pass through a catalyst; and
   wherein the second sensing element is between the first exhaust gas chamber and the second exhaust gas chamber in receipt of exhaust gas that has passed through the catalyst.

6. The sensor probe of claim 5, further comprising first leads extending from the electrodes of the first sensing element and second leads extending from the electrodes of the second sensing element, the first and second leads extend to an engine control unit that monitors current changes of the first sensing element and the second sensing element.

7. The sensor probe of claim 5, further comprising: a first diffusion layer through which exhaust gas flows into the first exhaust gas chamber; and a second diffusion layer through which exhaust gas flows into the second exhaust gas chamber.

8. The sensor probe of claim 5, further comprising a probe tip including the first sensing element, the second sensing element, the reference air chamber, the first exhaust gas chamber, and the second exhaust gas chamber.

9. The sensor probe of claim 5, wherein the sensor probe is connected to a vehicle exhaust line between a first catalyst brick and a second catalyst brick such that the second exhaust gas chamber is in receipt of exhaust gas that has passed through the first catalyst brick, and the first exhaust gas chamber is in receipt of exhaust gas that has not passed through the first catalyst brick and has been routed around the first catalyst brick through a bypass.

10. The sensor probe of claim 1, further comprising a heating element that heats the first sensing element and the second sensing element.

11. A sensor probe comprising:
    a first sensing element between a reference air chamber and a pre-catalyst exhaust gas chamber, the first sensing element generates current changes in response to changes in a relative amount of a target element present in reference air in the reference air chamber versus how much of the target element is present in exhaust gas of the pre-catalyst exhaust gas chamber; and
    a second sensing element between the pre-catalyst exhaust gas chamber and a post-catalyst exhaust gas chamber, the second sensing element generates current changes in response to changes in a relative amount of the target element present in exhaust gas of the pre-catalyst exhaust gas chamber versus how much of the target element is present in exhaust gas of the post-catalyst exhaust gas chamber.

12. The sensor probe of claim 11, wherein the target element is one of oxygen or $NO_x$.

13. The sensor probe of claim 11, wherein the first sensing element and the second sensing element both include a zirconia membrane coated with gas permeable electrodes on opposite sides thereof.

14. The sensor probe of claim 11, further comprising a heating element that heats the first sensing element and the second sensing element;
   wherein the sensor probe is connected to a vehicle exhaust line between a first catalyst brick and a second catalyst brick such that the post-catalyst exhaust gas chamber is in receipt of exhaust gas that has passed through the first catalyst brick, and the pre-catalyst exhaust gas chamber is in receipt of exhaust gas that has not passed through the first catalyst brick and has been routed around the first catalyst brick through a bypass.

15. A sensor probe comprising:
   a first sensing element between a first reference air chamber and a post-catalyst exhaust gas chamber, the first sensing element generates current changes in response to changes in a relative amount of a target element present in air of the first reference air chamber versus how much of the target element is present in exhaust gas of the post-catalyst exhaust gas chamber; and
   a second sensing element between a second reference air chamber and a pre-catalyst exhaust gas chamber, the second sensing element generates current changes in response to changes in a relative amount of the target element present in air of the second reference air chamber versus how much of the target element is present in exhaust gas of the pre-catalyst exhaust gas chamber.

16. The sensor probe of claim 15, wherein the target element is one of oxygen or $NO_x$.

17. The sensor probe of claim 15, wherein the first sensing element and the second sensing element both include a zirconia membrane coated with gas permeable electrodes on opposite sides thereof.

18. The sensor probe of claim 15, further comprising first leads extending from the gas permeable electrodes of the first sensing element and second leads extending from the gas permeable electrodes of the second sensing element, the first and second leads extend to an engine control unit that monitors current changes of the first sensing element and the second sensing element.

19. The sensor probe of claim 15, further comprising a heating element that heats the first sensing element and the second sensing element.

20. The sensor probe of claim 15, wherein the sensor probe is connected to a vehicle exhaust line between a first catalyst brick and a second catalyst brick such that the post-catalyst exhaust gas chamber is in receipt of exhaust gas that has passed through the first catalyst brick, and the pre-catalyst exhaust gas chamber is in receipt of exhaust gas that has not passed through the first catalyst brick and has been routed around the first catalyst brick through a bypass.

* * * * *